United States Patent
Mizunashi (10) Patent No.: US 6,168,940 B1
(45) Date of Patent: Jan. 2, 2001

(54) PROTEIN HAVING ETHYLENEDIAMINE-N, N'-DISUCCINIC ACID:ETHYLENEDIAMINE LYASE ACITIVITY AND GENE ENCODING THE SAME

(75) Inventor: Wataru Mizunashi, Kanagawa (JP)

(73) Assignee: Nitto Chemical Industry Co., Ltd., Tokyo (JP)

( * ) Notice: Under 35 U.S.C. 154(b), the term of this patent shall be extended for 0 days.

(21) Appl. No.: 08/980,994

(22) Filed: Dec. 1, 1997

(30) Foreign Application Priority Data

Nov. 12, 1996 (JP) .................................................. 8-333018
Feb. 28, 1997 (JP) .................................................. 9-060077

(51) Int. Cl.[7] .............................. C12N 9/88; C12N 15/00; C12N 5/00; C12N 1/20
(52) U.S. Cl. ...................... 435/232; 435/320.1; 435/325; 435/252.3; 435/128; 435/109; 536/23.1; 536/23.2; 536/24.32
(58) Field of Search .................................. 435/325, 320.1, 435/128, 109, 232, 252.3; 536/23.1, 24.32, 23.2

(56) References Cited

U.S. PATENT DOCUMENTS 5,874,262  2/1999  Zähner et al. ........................ 435/128

FOREIGN PATENT DOCUMENTS

WO 9636725  11/1996  (WO) .

OTHER PUBLICATIONS

Nishikiori, T., et al., Production by Actinomycetes of (S,S)–N, N'–Ethylenediaminedisuccinicacid, an Inhibitor of Phospholipase C, Journal of Antiboitics, vol. 37, No. 1, pp. 426–427 (1984).

Hoyer, L., et al., The ARG4 gene of *Candida albicans*, Gene, vol. 142, pp. 213–218 (1994).

Schmidt, G. et al., GenBank Database, Accession No. X56135, Jul. 26, 1991.*

* cited by examiner

Primary Examiner—Ponnathapu Achutamurthy
Assistant Examiner—Peter P. Tung
(74) Attorney, Agent, or Firm—Davidson, Davidson & Kappel, LLC (57) ABSTRACT

The present specification relates to a DNA comprising a nucleotide sequence coding for a polypeptide having ethylenediamine-N,N'-disuccinic acid:ethylenediamine lyase activity, the polypeptide having the amino acid sequence of SEQ ID NO: 1 which may have a deletion, substitution or addition of at least one amino acid; a recombinant plasmid containing the DNA; a host transformed with the recombinant plasmid; and a method for producing a diaminoalkylene-N,N'-disuccinic acid using the transformed host. The present specification also relates to a polypeptide having ethylenediamine-N,N'-disuccinic acid:ethylenediamine lyase activity which has the amino acid sequence of SEQ ID NO: 1 that may have a deletion, substitution or addition of at least one amino acid.

11 Claims, 4 Drawing Sheets

SEQUENCE LISTING (1) GENERAL INFORMATION:

(iii) NUMBER OF SEQUENCES: 5

(2) INFORMATION FOR SEQ ID NO: 1:

(i) SEQUENCE CHARACTERISTICS:
        (A) LENGTH: 495 amino acids
        (B) TYPE: amino acid
        (D) TOPOLOGY: linear     (ii) MOLECULE TYPE: protein     (vi) ORIGINAL SOURCE:
        (A) ORGANISM: Brevundimonas sp.
        (B) STRAIN: TN-3

(ix) FEATURE:
        (B) LOCATION:1
        (D) OTHER INFORMATION: Xaa = Met or none     (xi) SEQUENCE DESCRIPTION: SEQ ID NO: 1:

```
Xaa Thr Pro His Asn Pro Asp Ala Thr Arg Ile Gly Arg Ala Lys Arg
1               5                   10                  15

Ala Lys Ala Pro Glu Phe Gln Glu Leu Tyr Asp Phe Glu Ala Ala Ala
            20                  25                  30

Leu Thr Leu Thr Ser Ala Val Phe Pro Tyr Asp Ser Lys Ile His Arg
        35                  40                  45

Ala His Val Val Met Leu Ala Glu Gln Asp Ile Leu Thr Arg Asp Glu
    50                  55                  60

Ala Ala Ser Ile Leu Asn Gly Leu Ala Lys Ala Asp Glu Leu Ala Gly
65                  70                  75                  80

Lys Asp Ala Ala Leu Arg Thr Tyr Leu Pro Tyr Glu Ala Ala Leu Lys
                85                  90                  95

Arg Glu Ile Gly Ser Val Ala Gly Lys Met His Ile Gly Arg Ser Ala
                100                 105                 110

Asn Asp Leu Arg Asn Arg Val Asn Ala Cys Ser Cys Val Thr Ala Leu
            115                 120                 125

Arg Thr Val Glu Ala Val Ile Ala Leu Arg Glu Ala Val Val Thr Lys
        130                 135                 140

Ala Ala Asp His Leu Asp Thr Val Met Val Tyr Thr Gln Arg Lys
145                 150                 155                 160

Glu Ala Gln Pro Ile Thr Leu Gly His Tyr Leu Met Ala Ile Ser Glu
                165                 170                 175

Asn Leu Gly Lys Asn Leu Ala Arg Tyr Arg Glu Leu His Pro Arg Ile
            180                 185                 190

Asn Gln Cys Pro Leu Gly Ala Ala Ala Thr Ala Gly Thr Gly Trp Pro
        195                 200                 205
```

Leu Asp Arg Asp Arg Thr Ala Ala Leu Leu Gly Phe His Gly Leu Val
    210                 215                 220

Val Asn Ser Ile Glu Gly Val Ala Gly Trp Asp His Val Ala Glu Phe
225                 230                 235                 240

Ala Phe Asp Asn Ala Val Phe Leu Ser Gly Leu Ser Arg Leu Ala Ser
                245                 250                 255

Glu Ile Gln Leu Trp Ser Thr Asp Glu Tyr Gln Met Ala Glu Leu Asp
                260                 265                 270

Ser Ala Phe Ala Gly Thr Ser Ser Ile Met Pro Gln Lys Lys Asn Pro
            275                 280                 285

Asp Ser Leu Glu Arg Ser Arg Lys Gly Ala Phe Ala Ala Met Gly Pro
    290                 295                 300

Leu Val Ala Ile Leu Thr Ser Leu Asn Gly Ile Glu Tyr Gln Tyr Ser
305                 310                 315                 320

Ala Ala Arg Val Glu Leu Glu Pro Arg Ser Ile Asp Ala Leu Ile Ala
                325                 330                 335

Ala Thr His Ala Met Thr Gly Val Val Arg Thr Leu His Pro Asn Lys
            340                 345                 350

Glu Gln Asp Ala Cys Ala Met Arg Gln Glu Asn Tyr Ala Thr Met Thr
    355                 360                 365

Asp Leu Thr Asp Leu Leu Val Arg Arg Ile Gly Ile Asp Tyr Arg Glu
370                 375                 380

Ala His Glu Ile Val Ala Arg Val Val Met Thr Ala Ile Glu Arg Gly
385                 390                 395                 400

Ile Lys Ala Asn Ala Ile Gly Leu Asp Leu Val Gln Glu Ala Ala Val
                405                 410                 415

Ala Gln Thr Gly Asn Arg Ile Glu Ile Gly Ala Ala Asp Ile Ala Asp
            420                 425                 430

Ala Leu Asp Pro Val Gln Asn Val Ala Arg Arg Lys Gly Arg Gly Met
    435                 440                 445

Pro Ala Pro Glu Ser Val Arg Ala Ala Ile Ala Glu Ala Arg Gln Glu
450                 455                 460

Leu Asp Ala Asp Lys Ala Trp Leu Glu Asp Arg Arg Ala Gly Leu Ala
465                 470                 475                 480

Asp Ala Asp Ala Ala Leu Glu Glu Ala Val Ala Gly Ile Thr Thr
                485                 490                 495

(2) INFORMATION FOR SEQ ID NO: 2:

(i) SEQUENCE CHARACTERISTICS:
        (A) LENGTH: 1922 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Brevundimonas sp.
        (B) STRAIN: TN-3

(ix) FEATURE:
        (A) NAME/KEY: CDS
        (B) LOCATION:176..1660

(xi) SEQUENCE DESCRIPTION: SEQ ID NO: 2:

GGATCCTCAT CAGCGAGCGC TTTCCGTCCG GCACCCGTAT TCTGCTGGAA GTCCTGCACA      60

GCAACCCCAA TGGCCGCACC TTCTGGGAGC GGATGGGGTT CGACCCCTAC GCGCTCTATC     120

-continued

| | |
|---|---|
| TCGAGCGGCG CGCCGGCCCC CTCACCTGAC CCTCAGACGA CTAGAGAAGA ACGCG ATG<br>                                                                       Met<br>                                                                        1 | 178 |
| ACC CCG CAT AAC CCA GAT GCC ACC CGT ATC GGC CGT GCC AAG CGC GCG<br>Thr Pro His Asn Pro Asp Ala Thr Arg Ile Gly Arg Ala Lys Arg Ala<br>         5            10          15 | 226 |
| AAG GCG CCG GAA TTC CAG GAA CTC TAT GAC TTC GAA GCA GCG GCA CTC<br>Lys Ala Pro Glu Phe Gln Glu Leu Tyr Asp Phe Glu Ala Ala Ala Leu<br>      20           25         30 | 274 |
| ACC CTG ACG AGC GCC GTC TTT CCT TAC GAC AGC AAG ATT CAT CGT GCT<br>Thr Leu Thr Ser Ala Val Phe Pro Tyr Asp Ser Lys Ile His Arg Ala<br> 35          40          45 | 322 |
| CAC GTC GTC ATG CTG GCT GAA CAG GAC ATC CTG ACC CGG GAC GAG GCT<br>His Val Val Met Leu Ala Glu Gln Asp Ile Leu Thr Arg Asp Glu Ala<br>50          55          60         65 | 370 |
| GCC AGC ATC CTG AAC GGG CTG GCC AAG GCG GAT GAA CTG GCG GGA AAG<br>Ala Ser Ile Leu Asn Gly Leu Ala Lys Ala Asp Glu Leu Ala Gly Lys<br>         70          75         80 | 418 |
| GAC GCG GCG CTG CGC ACC TAC CTG CCC TAT GAG GCC GCG CTG AAA CGC<br>Asp Ala Ala Leu Arg Thr Tyr Leu Pro Tyr Glu Ala Ala Leu Lys Arg<br>     85          90          95 | 466 |
| GAG ATC GGC TCC GTT GCC GGG AAG ATG CAT ATC GGG CGC AGT GCC AAC<br>Glu Ile Gly Ser Val Ala Gly Lys Met His Ile Gly Arg Ser Ala Asn<br>    100         105         110 | 514 |
| GAC CTC CGC AAT CGG GTA AAC GCA TGT TCC TGC GTG ACA GCT CTG CGC<br>Asp Leu Arg Asn Arg Val Asn Ala Cys Ser Cys Val Thr Ala Leu Arg<br>115         120          125 | 562 |
| ACC GTC GAG GCT GTG ATC GCA TTG CGC GAG GCA GTC GTG ACC AAG GCC<br>Thr Val Glu Ala Val Ile Ala Leu Arg Glu Ala Val Val Thr Lys Ala<br>130         135         140         145 | 610 |
| GCC GAC CAT CTC GAC ACG GTG ATG GTC GTC TAC ACC CAG CGC AAG GAG<br>Ala Asp His Leu Asp Thr Val Met Val Val Tyr Thr Gln Arg Lys Glu<br>         150         155         160 | 658 |
| GCC CAG CCG ATC ACG CTC GGC CAT TAC CTA ATG GCG ATC AGC GAA AAT<br>Ala Gln Pro Ile Thr Leu Gly His Tyr Leu Met Ala Ile Ser Glu Asn<br>     165         170         175 | 706 |
| CTG GGC AAG AAC CTC GCC CGC TAT CGC GAG CTC CAT CCG CGC ATC AAC<br>Leu Gly Lys Asn Leu Ala Arg Tyr Arg Glu Leu His Pro Arg Ile Asn<br>    180         185         190 | 754 |
| CAA TGT CCC CTC GGC GCC GCT GCC ACG GCG GGC ACG GGC TGG CCG CTG<br>Gln Cys Pro Leu Gly Ala Ala Ala Thr Ala Gly Thr Gly Trp Pro Leu<br>195         200         205 | 802 |
| GAT CGC GAC CGC ACC GCA GCA CTG CTG GGT TTC CAC GGG CTC GTC GTC<br>Asp Arg Asp Arg Thr Ala Ala Leu Leu Gly Phe His Gly Leu Val Val<br>210         215         220         225 | 850 |
| AAC AGC ATC GAG GGC GTG GCC GGC TGG GAC CAC GTC GCG GAA TTC GCC<br>Asn Ser Ile Glu Gly Val Ala Gly Trp Asp His Val Ala Glu Phe Ala<br>         230         235         240 | 898 |
| TTC GAC AAT GCC GTC TTC CTG AGC GGC CTC AGC CGC CTG GCT TCC GAG<br>Phe Asp Asn Ala Val Phe Leu Ser Gly Leu Ser Arg Leu Ala Ser Glu<br>     245         250         255 | 946 |
| ATC CAG CTC TGG AGC ACG GAC GAG TAT CAG ATG GCG GAA CTC GAC TCC<br>Ile Gln Leu Trp Ser Thr Asp Glu Tyr Gln Met Ala Glu Leu Asp Ser<br>    260         265         270 | 994 |
| GCC TTC GCC GGC ACC AGC AGC ATC ATG CCG CAG AAG AAA AAC CCG GAT<br>Ala Phe Ala Gly Thr Ser Ser Ile Met Pro Gln Lys Lys Asn Pro Asp<br>275         280         285 | 1042 |
| TCG CTG GAG CGC AGC CGG AAA GGC GCC TTC GCG GCG ATG GGG CCG CTG<br>Ser Leu Glu Arg Ser Arg Lys Gly Ala Phe Ala Ala Met Gly Pro Leu | 1090 |

-continued

```
            290                 295                 300                 305
GTC GCC ATC CTC ACC TCT CTC AAT GGT ATC GAG TAC CAG TAC AGC GCC           1138
Val Ala Ile Leu Thr Ser Leu Asn Gly Ile Glu Tyr Gln Tyr Ser Ala
                        310                 315                 320

GCC AGG GTC GAG CTC GAA CCG CGA TCC ATC GAT GCG CTG ATC GCG GCC           1186
Ala Arg Val Glu Leu Glu Pro Arg Ser Ile Asp Ala Leu Ile Ala Ala
            325                 330                 335

ACC CAC GCG ATG ACG GGC GTC GTG CGG ACG CTT CAT CCC AAC AAG GAG           1234
Thr His Ala Met Thr Gly Val Val Arg Thr Leu His Pro Asn Lys Glu
            340                 345                 350

CAA GAT GCT TGC GCT ATG CGG CAA GAG AAC TAC GCC ACC ATG ACC GAC           1282
Gln Asp Ala Cys Ala Met Arg Gln Glu Asn Tyr Ala Thr Met Thr Asp
            355                 360                 365

CTG ACC GAC CTG CTC GTC CGT CGC ATC GGC ATC GAC TAT CGC GAG GCC           1330
Leu Thr Asp Leu Leu Val Arg Arg Ile Gly Ile Asp Tyr Arg Glu Ala
370                 375                 380                 385

CAT GAG ATC GTG GCG CGC GTG GTG ATG ACG GCG ATC GAG CGC GGC ATC           1378
His Glu Ile Val Ala Arg Val Val Met Thr Ala Ile Glu Arg Gly Ile
                390                 395                 400

AAG GCC AAC GCC ATC GGA CTG GAC CTC GTG CAG GAG GCC GCG GTC GCG           1426
Lys Ala Asn Ala Ile Gly Leu Asp Leu Val Gln Glu Ala Ala Val Ala
                405                 410                 415

CAG ACG GGC AAC CGG ATC GAG ATC GGT GCG GCC GAC ATC GCC GAT GCG           1474
Gln Thr Gly Asn Arg Ile Glu Ile Gly Ala Ala Asp Ile Ala Asp Ala
            420                 425                 430

CTC GAT CCG GTT CAG AAC GTC GCC CGT CGC AAG GGC AGG GGC ATG CCC           1522
Leu Asp Pro Val Gln Asn Val Ala Arg Arg Lys Gly Arg Gly Met Pro
435                 440                 445

GCG CCC GAA TCC GTC AGG GCC GCC ATC GCG GAG GCG CGT CAG GAA TTG           1570
Ala Pro Glu Ser Val Arg Ala Ala Ile Ala Glu Ala Arg Gln Glu Leu
450                 455                 460                 465

GAC GCC GAC AAG GCC TGG CTA GAG GAC CGG CGC GCC GGG CTG GCC GAT           1618
Asp Ala Asp Lys Ala Trp Leu Glu Asp Arg Arg Ala Gly Leu Ala Asp
                470                 475                 480

GCG GAT GCG GCG CTG GAG GAG GCG GTG GCC GGC ATC ACG ACC               1660
Ala Asp Ala Ala Leu Glu Glu Ala Val Ala Gly Ile Thr Thr
                485                 490                 495

TGAGGCCTGC TGCCTCCCTG CCGAAAATCT CGACTCGTGG TTCAAAAAAG AGGGGATAGC         1720

CATGACGAAG ACGGTTTTTT TCTATCTGCT GACGATGACT GCCGGCGCCA TGAGCGGCTT         1780

GACCGGAGCG GCGCATGGCC AAGCCATCAC CGTTCCCGCC GCGCTGAAGG AAAAAGGCGA         1840

GTTGCGTGTC GGCGTCAAAT GCGACACGCC GCCTGCCGGT TTCCTCGACG AAAAGGGTAA         1900

GCCCACCGGC ATCGATATCG AT                                                 1922
```

(2) INFORMATION FOR SEQ ID NO: 3:

(i) SEQUENCE CHARACTERISTICS:
        (A) LENGTH: 1488 base pairs
        (B) TYPE: nucleic acid
        (C) STRANDEDNESS: double
        (D) TOPOLOGY: linear     (ii) MOLECULE TYPE: DNA (genomic)

(vi) ORIGINAL SOURCE:
        (A) ORGANISM: Brevundimonas sp.
        (B) STRAIN: TN-3

(ix) FEATURE:
        (A) NAME/KEY: CDS
        (B) LOCATION:1..1488

(xi) SEQUENCE DESCRIPTION: SEQ ID NO: 3:

```
ATG ACC CCG CAT AAC CCA GAT GCC ACC CGT ATC GGC CGT GCC AAG CGC        48
Met Thr Pro His Asn Pro Asp Ala Thr Arg Ile Gly Arg Ala Lys Arg
 1               5                  10                  15

GCG AAG GCG CCG GAA TTC CAG GAA CTC TAT GAC TTC GAA GCA GCG GCA        96
Ala Lys Ala Pro Glu Phe Gln Glu Leu Tyr Asp Phe Glu Ala Ala Ala
                20                  25                  30

CTC ACC CTG ACG AGC GCC GTC TTT CCT TAC GAC AGC AAG ATT CAT CGT       144
Leu Thr Leu Thr Ser Ala Val Phe Pro Tyr Asp Ser Lys Ile His Arg
         35                  40                  45

GCT CAC GTC GTC ATG CTG GCT GAA CAG GAC ATC CTG ACC CGG GAC GAG       192
Ala His Val Val Met Leu Ala Glu Gln Asp Ile Leu Thr Arg Asp Glu
     50                  55                  60

GCT GCC AGC ATC CTG AAC GGG CTG GCC AAG GCG GAT GAA CTG GCG GGA       240
Ala Ala Ser Ile Leu Asn Gly Leu Ala Lys Ala Asp Glu Leu Ala Gly
 65                  70                  75                  80

AAG GAC GCG GCG CTG CGC ACC TAC CTG CCC TAT GAG GCC GCG CTG AAA       288
Lys Asp Ala Ala Leu Arg Thr Tyr Leu Pro Tyr Glu Ala Ala Leu Lys
                85                  90                  95

CGC GAG ATC GGC TCC GTT GCC GGG AAG ATG CAT ATC GGG CGC AGT GCC       336
Arg Glu Ile Gly Ser Val Ala Gly Lys Met His Ile Gly Arg Ser Ala
                100                 105                 110

AAC GAC CTC CGC AAT CGG GTA AAC GCA TGT TCC TGC GTG ACA GCT CTG       384
Asn Asp Leu Arg Asn Arg Val Asn Ala Cys Ser Cys Val Thr Ala Leu
         115                 120                 125

CGC ACC GTC GAG GCT GTG ATC GCA TTG CGC GAG GCA GTC GTG ACC AAG       432
Arg Thr Val Glu Ala Val Ile Ala Leu Arg Glu Ala Val Val Thr Lys
     130                 135                 140

GCC GCC GAC CAT CTC GAC ACG GTG ATG GTC GTC TAC ACC CAG CGC AAG       480
Ala Ala Asp His Leu Asp Thr Val Met Val Val Tyr Thr Gln Arg Lys
145                 150                 155                 160

GAG GCC CAG CCG ATC ACG CTC GGC CAT TAC CTA ATG GCG ATC AGC GAA       528
Glu Ala Gln Pro Ile Thr Leu Gly His Tyr Leu Met Ala Ile Ser Glu
                165                 170                 175

AAT CTG GGC AAG AAC CTC GCC CGC TAT CGC GAG CTC CAT CCG CGC ATC       576
Asn Leu Gly Lys Asn Leu Ala Arg Tyr Arg Glu Leu His Pro Arg Ile
                180                 185                 190

AAC CAA TGT CCC CTC GGC GCC GCT GCC ACG GCG GGC ACG GGC TGG CCG       624
Asn Gln Cys Pro Leu Gly Ala Ala Ala Thr Ala Gly Thr Gly Trp Pro
         195                 200                 205

CTG GAT CGC GAC CGC ACC GCA GCA CTG CTG GGT TTC CAC GGG CTC GTC       672
Leu Asp Arg Asp Arg Thr Ala Ala Leu Leu Gly Phe His Gly Leu Val
     210                 215                 220

GTC AAC AGC ATC GAG GGC GTG GCC GGC TGG GAC CAC GTC GCG GAA TTC       720
Val Asn Ser Ile Glu Gly Val Ala Gly Trp Asp His Val Ala Glu Phe
225                 230                 235                 240

GCC TTC GAC AAT GCC GTC TTC CTG AGC GGC CTC AGC CGC CTG GCT TCC       768
Ala Phe Asp Asn Ala Val Phe Leu Ser Gly Leu Ser Arg Leu Ala Ser
                245                 250                 255

GAG ATC CAG CTC TGG AGC ACG GAC GAG TAT CAG ATG GCG GAA CTC GAC       816
Glu Ile Gln Leu Trp Ser Thr Asp Glu Tyr Gln Met Ala Glu Leu Asp
                260                 265                 270

TCC GCC TTC GCC GGC ACC AGC AGC ATC ATG CCG CAG AAG AAA AAC CCG       864
Ser Ala Phe Ala Gly Thr Ser Ser Ile Met Pro Gln Lys Lys Asn Pro
         275                 280                 285

GAT TCG CTG GAG CGC AGC CGG AAA GGC GCC TTC GCG GCG ATG GGG CCG       912
Asp Ser Leu Glu Arg Ser Arg Lys Gly Ala Phe Ala Ala Met Gly Pro
     290                 295                 300

CTG GTC GCC ATC CTC ACC TCT CTC AAT GGT ATC GAG TAC CAG TAC AGC       960
Leu Val Ala Ile Leu Thr Ser Leu Asn Gly Ile Glu Tyr Gln Tyr Ser
```

```
Leu Val Ala Ile Leu Thr Ser Leu Asn Gly Ile Glu Tyr Gln Tyr Ser
305                 310                 315                 320

GCC GCC AGG GTC GAG CTC GAA CCG CGA TCC ATC GAT GCG CTG ATC GCG      1008
Ala Ala Arg Val Glu Leu Glu Pro Arg Ser Ile Asp Ala Leu Ile Ala
                325                 330                 335

GCC ACC CAC GCG ATG ACG GGC GTC GTG CGG ACG CTT CAT CCC AAC AAG      1056
Ala Thr His Ala Met Thr Gly Val Val Arg Thr Leu His Pro Asn Lys
                340                 345                 350

GAG CAA GAT GCT TGC GCT ATG CGG CAA GAG AAC TAC GCC ACC ATG ACC      1104
Glu Gln Asp Ala Cys Ala Met Arg Gln Glu Asn Tyr Ala Thr Met Thr
            355                 360                 365

GAC CTG ACC GAC CTG CTC GTC CGT CGC ATC GGC ATC GAC TAT CGC GAG      1152
Asp Leu Thr Asp Leu Leu Val Arg Arg Ile Gly Ile Asp Tyr Arg Glu
    370                 375                 380

GCC CAT GAG ATC GTG GCG CGC GTG GTG ATG ACG GCG ATC GAG CGC GGC      1200
Ala His Glu Ile Val Ala Arg Val Val Met Thr Ala Ile Glu Arg Gly
385                 390                 395                 400

ATC AAG GCC AAC GCC ATC GGA CTG GAC CTC GTG CAG GAG GCC GCG GTC      1248
Ile Lys Ala Asn Ala Ile Gly Leu Asp Leu Val Gln Glu Ala Ala Val
                405                 410                 415

GCG CAG ACG GGC AAC CGG ATC GAG ATC GGT GCG GCC GAC ATC GCC GAT      1296
Ala Gln Thr Gly Asn Arg Ile Glu Ile Gly Ala Ala Asp Ile Ala Asp
                420                 425                 430

GCG CTC GAT CCG GTT CAG AAC GTC GCC CGT CGC AAG GGC AGG GGC ATG      1344
Ala Leu Asp Pro Val Gln Asn Val Ala Arg Arg Lys Gly Arg Gly Met
                435                 440                 445

CCC GCG CCC GAA TCC GTC AGG GCC GCC ATC GCG GAG GCG CGT CAG GAA      1392
Pro Ala Pro Glu Ser Val Arg Ala Ala Ile Ala Glu Ala Arg Gln Glu
        450                 455                 460

TTG GAC GCC GAC AAG GCC TGG CTA GAG GAC CGG CGC GCC GGG CTG GCC      1440
Leu Asp Ala Asp Lys Ala Trp Leu Glu Asp Arg Arg Ala Gly Leu Ala
465                 470                 475                 480

GAT GCG GAT GCG GCG CTG GAG GAG GCG GTG GCC GGC ATC ACG ACC TGA      1488
Asp Ala Asp Ala Ala Leu Glu Glu Ala Val Ala Gly Ile Thr Thr
                485                 490                 495
```

(2) INFORMATION FOR SEQ ID NO: 4:

(i) SEQUENCE CHARACTERISTICS:
  (A) LENGTH: 23 base pairs
  (B) TYPE: nucleic acid
  (C) STRANDEDNESS: single
  (D) TOPOLOGY: linear  (ii) MOLECULE TYPE: other nucleic acid
  (A) DESCRIPTION: /desc = "synthetic DNA"

(ix) FEATURE:
  (B) LOCATION:6
  (D) OTHER INFORMATION: N = Inosine or any one of A, C, G and T  (ix) FEATURE:
  (B) LOCATION:9
  (D) OTHER INFORMATION: N = Inosine or any one of A, C, G and T  (ix) FEATURE:
  (B) LOCATION:18
  (D) OTHER INFORMATION: N = Inosine or any one of A, C, G and T  (xi) SEQUENCE DESCRIPTION: SEQ ID NO: 4:

ATGACNCCNC AYAAYCCNGA YGC            23

(2) INFORMATION FOR SEQ ID NO: 5:

(i) SEQUENCE CHARACTERISTICS:

```
        (A) LENGTH: 34 base pairs
        (B) TYPE: nucleic acid
        (C) STRANDEDNESS: single
        (D) TOPOLOGY: linear (ii) MOLECULE TYPE: other nucleic acid
         (A) DESCRIPTION:   /desc = "synthetic DNA"

(ix) FEATURE:
         (B) LOCATION:14
         (D) OTHER INFORMATION: N = Inosine or any one of A, C, G and T (ix) FEATURE:
         (B) LOCATION:17
         (D) OTHER INFORMATION: N = Inosine or any one of A, C, G and T (ix) FEATURE:
         (B) LOCATION:23
         (D) OTHER INFORMATION: N = Inosine or any one of A, C, G and T (ix) FEATURE:
         (B) LOCATION:26
         (D) OTHER INFORMATION: N = Inosine or any one of A, C, G and T (xi) SEQUENCE DESCRIPTION: SEQ ID NO: 5:

CCDATYTCAT YTTNCCNGCR ACNGANCCDA TYTC                                          34
```

PROTEIN HAVING ETHYLENEDIAMINE-N, N'-DISUCCINIC ACID:ETHYLENEDIAMINE LYASE ACITIVITY AND GENE ENCODING THE SAME

BACKGROUND OF THE INVENTION

This application claims priority from Japanese Patent Application No. 333018/1996, filed Nov. 29, 1996 and Japanese Patent Application 60077/1997, filed Feb. 28, 1997.

The present invention relates to a protein having ethylenediamine-N,N'-disuccinic acid: ethylenediamine lyase activity and a gene coding for the protein.

Diaminoalkylene-N,N'-disuccinic acids are not only important as intermediates for synthesis of medicines and agricultural chemicals but also unique in terms of having an ability to capture heavy metals. Also, since optical isomers of these compounds are expected to have a possibility of being susceptible to biodegradation when they have been released to the natural world, these compounds may be used as a chelating agent, a builder for detergent, etc.

Diaminoalkylene-N,N'-disuccinic acids can be synthesized easily from various amines and maleic or fumaric acid. However, in the case of optically active diaminoalkylene-N,N'-disuccinic acids, optically active aspartic acid or the like is needed as a starting material for the organosynthesis of such compounds. For example, optically active diaminoethylene-N,N'-disuccinic acid can be prepared from L-aspartic acid and dibromoethane [John A. Neal et al., Inorganic Chem. 7, 2405 (1968)]. However, L-aspartic acid and dibromoethane are relatively expensive raw materials and, thus, the product prepared from these materials cannot be supplied in various fields at a low cost.

On the other hand, diaminoalkylene-N,N'-disuccinic acids have also been isolated and identified from culture solutions of some actinomycetes [T. Nishikiori et al., J. Antibiotics 37, 426 (1984)]. However, the productivity of these actinomycetes is extremely low and, thus, a method of producing a diaminoalkylene-N,N'-disuccinic acid using such a bacterium is not practical in industry.

Under these circumstances, the inventor has previously proposed a novel method for efficiently producing optically active S,S-diaminoalkylene-N,N'-disuccinic acids from fumaric or maleic acid and various diamines by utilizing a catalytic action of microorganisms (Japanese Unexamined Patent Publication No. 9-140390; EP-0731171A; EP-0805211A).

It is an object of the present invention to further improve the catalytic action of the microorganisms.

SUMMARY OF THE INVENTION

The inventor has succeeded in improving the yield of a diaminoalkylene-N,N'-disuccinic acid in microorganism cells by cloning a gene for an ethylenediamine-N,N'-disuccinic acid:ethylenediamine lyase and allowing multiple copies of this gene to exist in cells of a microorganism by genetic recombination to thereby enhance the catalytic ability of the microorganism greatly. Thus, the present invention has been achieved.

The invention provides a DNA comprising a nucleotide sequence coding for a polypeptide having ethylenediamine-N,N'-disuccinic acid: ethylenediamine lyase activity, the polypeptide having the amino acid sequence of SEQ ID NO: 1 which may have a deletion, substitution or addition of at least one amino acid. The DNA comprising a nucleotide sequence coding for a polypeptide having ethylenediamine-N,N'-disuccinic acid:ethylenediamine lyase activity may be a DNA comprising a nucleotide sequence coding for a polypeptide having the amino acid sequence of SEQ ID NO: 1 or its analogue derived from the degeneracy of genetic codes. The nucleotide sequence coding for the polypeptide may have the nucleotide sequence of SEQ ID NO: 2.

In another aspect of the invention, the invention provides a DNA which hybridizes with the nucleotide sequence of SEQ ID NO: 2 or a fragment thereof and which comprises a nucleotide sequence coding for a polypeptide having ethylenediamine-N,N'-disuccinic acid: ethylenediamine lyase activity. Examples of the fragment of the nucleotide sequence of SEQ ID NO: 2 include a fragment of 326 bases ranging from nucleotide No. 176 to nucleotide No. 501 in the nucleotide sequence of SEQ ID NO: 2. The hybridization may be performed at 25–40° C. and at a formamide concentration of 10–50%. The conditions of washing may be appropriately determined depending on the detection method to be used.

Furthermore, the invention also provides a DNA fragment of 200–350 bp which can be amplified with synthetic DNAs consisting of the nucleotide sequences of SEQ ID NOS: 4 and 5, respectively. This DNA fragment can be used for obtaining a gene analogue to the ethylenediamine-N,N'-disuccinic acid:ethylenediamine lyase gene or for judging whether a gene obtained is identical with the ethylenediamine-N,N'-disuccinic acid:ethylenediamine lyase gene or not.

The invention also provides a recombinant plasmid containing the DNA comprising a nucleotide sequence coding for a polypeptide having ethylenediamine-N,N'-disuccinic acid:ethylenediamine lyase activity.

The invention further provides a host transformed with the recombinant plasmid. The host may be a microorganism such as *E. coli*. The transformed host can be used to produce diaminoalkylene-N,N'-disuccinic acid and, thus, the invention also provides a method for producing diaminoalkylene-N,N'-disuccinic acid using the transformed host.

Moreover, the invention provides a polypeptide having ethylenediamine-N,N'-disuccinic acid:ethylenediamine lyase activity which has the amino acid sequence of SEQ ID NO: 1 that may have a deletion, substitution or addition of at least one amino acid. The deletion, substitution or addition can be performed by a well-known technique, site-specific mutagenesis (see, for example, Nucleic Acid Research, Vol. 10, No. 20, pp. 6487–6500, 1982).

The cloned ethylenediamine-N,N'-disuccinic acid:ethylenediamine lyase gene can be introduced in multiple copies into microorganism cells by genetic recombination. Thus, it is possible to enhance the catalytic ability of the microorganism greatly to thereby improve the yield of a diaminoalkylene-N,N'-disuccinic acid.

DESCRIPTION OF THE PREFERRED EMBODIMENT

Hereinbelow, the invention will be described in detail.

The "ethylenediamine-N,N'-disuccinic acid:ethylenediamine lyase" used herein is a generic term for a group of enzymes which have an ability to reversibly produce ethylenediamine-N,N'-disuccinic acid from fumaric acid and ethylenediamine. However, this enzyme may produce ethylenediamine-N-monosuccinic acid depending on reaction conditions. Furthermore, this enzyme also exhibits reactivity with those diamines other than ethylenediamine to produce corresponding diaminoalkylene-N,N-disuccinic acids. The diaminoalkylene-N,N-disuccinic acids thus produced are optically active compounds in many cases, but some enzymes of this group produce racemic compounds.

A group of enzymes exhibiting such reactivity have been found in those bacteria belonging to plurality of genuses which have been separated from the natural world and identified by the inventor and co-workers. These bacteria are disclosed in Japanese Unexamined Patent Publication No. 9-140390 (corresponding to EP-0731171A, EP-0805211A), supra.

The invention relates to an ethylenediamine-N,N'-disuccinic acid: ethylenediamine lyase gene derived from Brevundixonas sp. TN-3 disclosed in EP-0805211A Brevundimonas sp. TN-3 was deposited on Apr. 11, 1996, with the National Institute of Bioscience and Human Technology Agency of Industrial Science and Technology, 1–3, Higashi 1-chome, Tsukuba-shi, Ibaraki-ken, 305 Japan. The deposit is under Accession No. FERM BP-5886.

One embodiment of the invention will be described below. In the following steps, any appropriate techniques or materials known in the art may be used.

(1) Preparation of Chromosomal DNA from Strain TN-3

Chromosomal DNA is separated and prepared from strain TN-3.

(2) Preparation of Purified Enzyme

An ethylenediamine-N,N'-disuccinic acid:ethylenediamine lyase protein is purified from strain TN-3.

(3) Analysis of Amino Acid Sequences of the N-Terminus and Inner Peptide of the Purified Enzyme For the purified ethylenediamine-N,N'-disuccinic acid: ethylenediamine lyase protein, the amino acid sequences of its N-Terminus and its inner peptide are analyzed.

(4) Preparation of Probe

Nucleotide sequences are presumed from the amino acid sequences of the N-terminus and the inner peptide and two synthetic DNAs are prepared. These synthetic DNAs are used as primers to perform a polymerase chain reaction (PCR) using the chromosomal DNA from strain TN-3 as a template. As a result, a portion of the ethylenediamine-N, N'-disuccinic acid:ethylenediamine lyase gene are amplified to produce a DNA fragment.

(5) Preparation of DNA Library

The chromosomal DNA is digested with restriction enzymes and then the resultant fragments are inserted into plasmid vector pUC18 to prepare a library.

(6) Preparation of E. coli Transformants and Selection of a Recombinant DNA

E. coli transformants are prepared with the DNA library from step (5) above. Then, a transformant containing a recombinant DNA of interest is selected by colony hybridization using the DNA fragment from step (4) above as a probe.

(7) Preparation of Recombinant Plasmid

A plasmid is prepared from the transformant selected in step (6) above.

(8) Preparation of Restriction Map and Identification of the Ethylenediamine-N,N'-Disuccinic Acid:Ethylenediamine Lyase Gene Region For the recombinant plasmid from step (7) above, a restriction map is prepared and a region with which the probes hybridize is specified.

(9) Determination of Nucleotide Sequences

Nucleotide sequences of regions around the region identified in step (8) are determined.

(10) Production of Ethylenediamine-N,N'-Disuccinic Acid

A region containing the ethylenediamine-N,N'-disuccinic acid: ethylenediamine lyase gene is cut out from the recombinant plasmid from step (7) above and inserted into vector pUC119 for E. coli. The resultant recombinant plasmid is introduced into E. coli strain JM109, and this transformed E. coli is cultured in an appropriate medium under appropriate culture conditions. Cells are separated from the resultant culture solution and used to perform a reaction of fumaric acid and ethylenediamine as starting materials. The product, ethylenediamine-N,N'-disuccinic acid produced is isolated/purified.

Strain TN-3 has been deposited with the National Institute of Bioscience and Human-technology, Agency of Industrial Science and Technology under the Accession No. FERM BP-5886 as being designated Brevundimonas sp. TN-3. Its bacteriological properties are as follows.

Bacteriological Properties of Strain TN-3
Morphology: bacillus
Gram stain: −
Spores: −
Mobility: +
Flagella: polar flagellation
Oxygen requirement: aerobic
Oxidase: +
Catalase: +
OF test: −
Color tone of colonies: No characteristic pigment is generated.
Production of fluorescent pigment: −
Accumulation of PHB: +
Auxotrophy: present
Quinone system: Q-10
Reduction of nitrates: +
Production of Indole: −
Arginine dihydrolase: −
Urea degradation: −
Esculin degradation: −
Gelatin liquefaction: −
PNPG: −
Assimilation:
   Glucose −
   L-Arabinose −
   D-Mannose −
   D-Mannitol −
   N-Acetyl-D-glucosamine −
   Maltose −
   Potassium gluconate +
   n-Capric acid −
   Adipic acid +
   d1-Malic acid +
   Citric acid +
   Phenyl acetate −

Hereinbelow, the invention will be described in more detail with reference to the following Examples. However, the scope of the invention is not limited by these Examples.

EXAMPLE 1

(1) Preparation of Chromosomal DNA from Strain TN-3

Strain TN-3 was cultured with shaking in 100 ml of an EDDS medium [0.2% ethylenediamine-N,N'-disuccinic acid, 0.2% glucose, 0.1% bacto-yeast extract, 0.05% Polypeptone, 0.1% $MgSO_4.7H_2O$, 2.5% (v/v) phosphate buffer (1M, pH 7.0), a 0.5% (v/v) solution of metal salt mixture (containing 56 g of $NaSO_4$, 8 g of $MgCl_2.6H2O$, 0.8 g of $CaCl_2$, 0.6 g of $MgSO_4.4H_2O$, 0.12 g of $FeCl_3.6H_2O$ and 0.06 g of $ZnSO_4$ per 100 ml)] at 30° C. for 4 days. Then, cells were harvested and suspended in 4 ml of a saline-EDTA solution (0.1 M EDTA, 15 M NaCl, pH 8.0), followed by addition of 8 mg of lysozyme. The resultant suspension was shaken at 37° C. for 1 hour and then frozen. Subsequently, 10 ml of a Tris-SDS solution (1% SDS, 0.1 M NaCl, 0.1 M Tris, pH 9.0) was gently added thereto with shaking. Further, proteinase K (Merck) was added (the final concentration: 1 mg) thereto and shaken at 37° C. for 1 hour. Subsequently, an equal volume of TE-saturated phenol (TE:10 mM Tris, 1 mM EDTA, pH 8.0) was added to the solution and stirred. Then, the resultant solution was centrifuged to collect the upper layer, to which two volumes of ethanol was added. DNA was rolled round a glass rod, and the phenol was removed therefrom by washing with 80% and 70% ethanol in turn. Subsequently, the DNA was dissolved in 3 ml of a TE buffer, to which a ribonuclease A solution (heat-treated at 100° C. for 15 min.) was added to give a concentration of 10 mg/ml. The resultant mixture was shaken at 37° C. for 30 min. Proteinase K was further added to the solution and the mixture was shaken at 37° C. for 30 min. Then, an equal volume of TE-saturated phenol was added thereto and centrifuged to thereby separated the solution into the upper and the lower layers. The same procedure was repeated twice with the upper layer. Then, an equal volume of a chloroform solution (containing 4% isoamyl alcohol) was added to thereto, and the same extraction operation was repeated (hereinafter, these procedures are referred to as "phenol treatment"). Thereafter, two volumes of ethanol was added to the upper layer to recover the DNA by rolling it round a glass rod. Thus, a chromosomal DNA sample was obtained.

(2) Preparation of Purified Enzyme

Strain TN-3 was cultured with shaking in 2 L of an EDDS medium at 30° C. for 4 days. Then, cells were harvested, suspended in 100 ml of a 10 mM sodium phosphate buffer (pH 8.0, containing 1 mM dithiothreitol) and dispersed with an ultrasonic dispenser, followed by centrifugation at 12,000 rpm for 20 min. To the resultant supernatant, ammonium sulfate was added to give 30% saturation and left undisturbed at 4° C. for 30 min., followed by centrifugation. To the resultant supernatant, ammonium sulfate was added to give 60% saturation and left undisturbed at 4° C. for 30 min., followed by centrifugation. The resultant precipitate was dissolved in 10 ml of a 10 mM sodium phosphate buffer (pH 8.0, containing 1 mM dithiothreitol) to prepare a solution of a partially purified enzyme. This partially purified-enzyme solution was purified further by ion exchange chromatography. Briefly, the enzyme solution was applied to a column (φ10 mm×20 cm) packed with DEAE-sephacryl (Pharmacia) equilibrated with a 10 mM sodium phosphate buffer (pH 8.0) containing 1 mM dithiothreitol to allow adsorption. After the column was washed with 40 ml of the same buffer, the enzyme was eluted with a linear gradient of 0–0.6 M KCl to fractionate into 2 ml fractions. Those fractions exhibiting ethylenediamine-N,N'-disuccinic acid:ethylenediamine lyase activity were collected to obtain a solution of the purified enzyme. When this solution was analyzed by SDS-polyacrylamide gel electrophoresis, an almost homogeneous, single band of about 60,000 in molecular weight was detected.

(3) Analysis of the Amino Acid Sequences of the N-Terminus and Inner Peptide of the Purified Enzyme The purified enzyme obtained in step (2) was subjected to SDS-polyacrylamide gel electrophoresis directly or after trypsin digestion to thereby fractionate polypeptides. The fractionated polypeptides were then electroblotted onto a PVDF membrane (Immobilon Psq; Millipore). The blotted membrane was stained with Coomassie Brilliant Blue. The stained band was cut out and subjected to amino acid sequence analysis. The analysis of the amino acid was conducted with a Shimadzu PSQ-1 amino acid analyzer. The results are shown below.

a) N-Terminal amino acid sequence of the non-treated enzyme: (molecular weight: about 60,000)
(Met-)Thr-Pro-His-Asn-Pro-Asp-Ala (amino acid 1–8 of SEQ ID NO:1)

b) Partial digest after the Trypsin digestion: (molecular weight: about 50,000)
Glu-Ile-Gly-Ser-Val-Gly-Lys-Met-Glu-Ile-Gly-Arg-Xaa-Ala-Asn-AsP-Leu-Arg-Asn-Arg (amino acid 98–118 of SEQ ID NO:1)

c) Partial digest after the Trypsin digestion: (molecular weight: about 10,000)
Ala-Ser-Gly-Ala-Lys-Ala-Pro-Glu-Phe-Gln-Glu-Leu-Tyr-Asp-Phe-Glu-Ala-Ala-Xaa-Leu-Xaa-Leu (amino acid 14–36 SEQ ID NO:1)

(The molecular weights of fractionated peptides are shown in parentheses. "Xaa" represents an amino acid which could not be identified in the analysis.)

(4) Preparation of Probe

Based on the amino acid sequence information from step (3) above, the respective synthetic DNAs of SEQ ID NOS: 4 and 5 were prepared as primers #1 and #2. A PCR was performed with these primers using the chromosomal DNA of strain TN-3 from step (1) as a template.

Briefly, 1 µl of the TN-3 chromosomal DNA, 10 µl of a 10×reaction buffer, 4 µl of 10 mM dNTP, 1 µl (equivalent to 100 pmol) each of primers #1 and #2, and 1 µl of ExTaq (Takara Shuzo) were mixed to give a total volume of 100 µl. This solution was incubated sequentially at 95° C. for 30 sec. (denaturing step), at 55° C. for 30 sec. (annealing step) and at 72° C. for 2 min. (extension step) in 30 cycles. After the completion of the reaction, the reaction solution was subjected to chloroform extraction (3 times) and ethanol precipitation to recover the amplified DNA. This DNA was separated by 1.0% agarose gel electrophoresis to obtain a DNA fragment of about 300 bp which is believed to encode the ethylenediamine-N,N'-disuccinic acid:ethylenediamine lyase gene of strain TN-3. The DNA fragment thus obtained was labeled with DIG DNA Labeling Kit (Boehringer Mannheim K. K.) to prepare a probe.

(5) Preparation of DNA Library

To 10 µl of the TN-3 chromosomal DNA, 5µl of a 10×restriction enzyme reaction buffer, 33 µl of sterilized water, 2 µl of restriction enzyme KpnI were added and the mixture was reacted at 37° C. for 16 hours. Thereafter, the DNA was recovered by ethanol precipitation and agarose gel electrophoresed. DNA fragments with sizes ranging from 6.5 kb to 5.5 kb were cut out from the gel and recovered with DNA PREP (DIA-IATRON). These DNA fragments were inserted into the KpnI site of vector pUC18 for E. coli using a ligation kit to prepare a recombinant DNA library.

The pUC18 fragment used in the above ligation was prepared as follows. To 2 μl of a stock solution of pUC18, 5 μl of a 10×restriction enzyme buffer, 40 μl of sterilized water and 3 μl of restriction enzyme KpnI were added and the mixture was reacted at 37° C. for 2 hours. Then, after phenol treatment and ethanol precipitation, the resultant DNA was dried and dissolved in 50 μl of sterilized water. To this solution, 1 μl of alkaline phosphatase (Takara Shuzo), 10 μl of a 10×buffer and 39 μl of sterilized water were added and the mixture was reacted at 65° C. Then, phenol treatment and ethanol precipitation were conducted. The resultant DNA fragments were dried and dissolved in sterilized water.

(6) Preparation of E. coli Transformant and Selection of Recombinant DNA

E. coli strain JM109 was inoculated into 1 ml of an LB medium (1% Bacto-Tryptone, 0.5% bacto-yeast extract, 0.5% NaCl) and pre-cultured at 37° C. for 5 hours under aerobic conditions. One hundred milliliters of this culture was added to 40 ml of an SOB medium (2% Bacto-Tryptone, 0.5% bacto-yeast extract, 10 mM NaCl, 2.5 mM KCl, 1 mM $MgSO_4$, 1 mM $MgCl_2$) and cultured at 18° C. for 20 hours. This culture was centrifuged to harvest cells. Then, 13 ml of a cool TF solution [20 mM PIPES-KOH (pH 6.0), 200 mM KCl, 10 mM $CaCl_2$, 40 mM $MnCl_2$] was added to the cells, and the mixture was left to stand at 0° C. for 10 min. Thereafter, the mixture was centrifuged again. After removal of the supernatant, precipitated E. coli cells were suspended in 3.2 ml of a cool TF solution, to which 0.22 ml of dimethyl sulfoxide was added. The resultant suspension was left to stand at 0° C. for 10 min. To 200 μl of the thus prepared competent cells, 10 μl of the recombinant plasmid-containing solution (DNA library) prepared in step (5) was added, and the resultant mixture was left to stand at 0° C. for 30 min. Then, a heat shock was given to the mixture at 42° C. for 30 sec., and the mixture was cooled at 0° C. for 2 min. One milliliter of an SOC medium (20 mM glucose, 2% Bacto-Tryptone, 0.5% bacto-yeast extract, 10 mM NaCl, 2.5 mM KCl, 1 mM $MgSO_4$, 1 mM $MgCl_2$) was added thereto, and the cells were cultured with shaking at 37° C. for 1 hour. This culture was seeded in 200 aliquots in an LB agar medium containing 100 μg/ml ampicillin and cultured at 37° C. The transformant colonies formed on the agar medium were examined by colony hybridization to select those transformants containing the ethylenediamine-N,N'-disuccinic acid:ethylenediamine lyase gene. Briefly, the transformants formed on the agar medium were transferred onto a nylon membrane (BIODYNE A: Pall Biosupport). DNA was fixed on the membrane by lysing cells and hybridized with the probe (of about 300 bp) from step (4) above. Then, colonies containing the recombinant DNA of interest were selected using DIG Luminescent Detection Kit (Boehringer Mannheim K. K.).

(7) Preparation of Recombinant Plasmid

The transformant selected in step (6) above was cultured in 100 ml of an LB medium at 37° C. overnight. Then, cells were harvested and washed with sterilized water. To the cells, 5 ml of solution I [2 mM glucose, 10 mM EDTA, 25 mM Tris-HCl (pH 8.0)] and 25 mg of lysozyme were added, and the resultant mixture was left to stand at 0° C. for 30 min. Then, 10 ml of solution II (1 N NaOH, 5% SDS) was added thereto, and the mixture was left to stand at 0° C. for 5 min. Thereafter, 7.5 ml of solution III [3 M sodium acetate (pH 4.8)] was added, and the mixture was left to stand at 0° C. for 30 min. This mixture was centrifuged to obtain the supernatant, to which 50 ml of ethanol was added. The mixture was centrifuged and the resultant supernatant was discarded. To the residue, 5 ml of solution IV [10 mM sodium acetate, 50 mM Tris-HCl (pH 8.0)] and 2.5 μl of ribonuclease solution A (10 mg/ml) were added, and the mixture was left to stand at room temperature for 20 min. Then, 12 ml of ethanol was added thereto. The plasmid was recovered by centrifugation, rinsed with 70% ethanol, dried and dissolved in 0.4 ml of sterilized water. The thus obtained recombinant plasmid was designated pEDS001.

Figure 1:
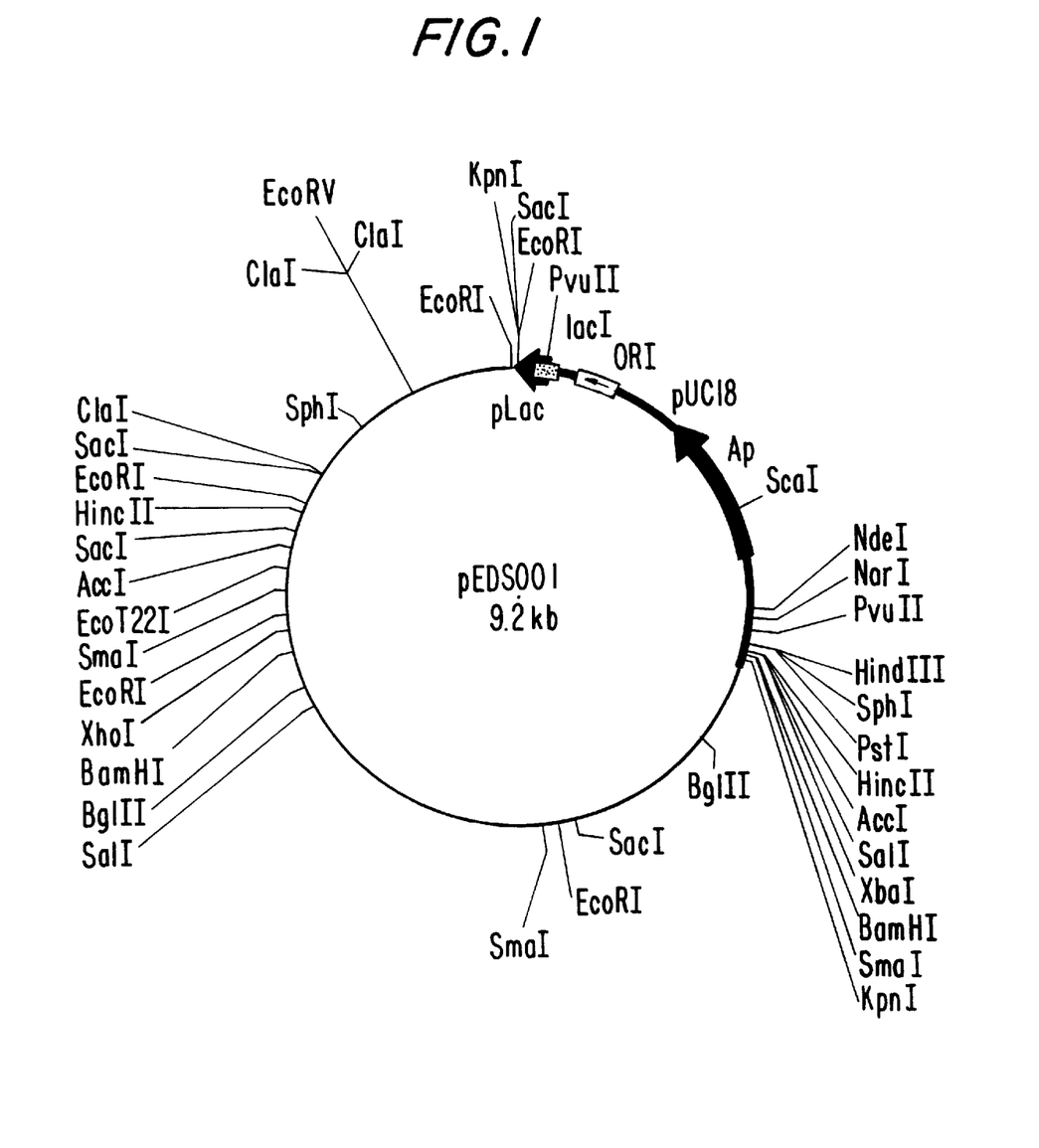
FIG. 1 is a restriction map for plasmid pEDS.001.
Figure 2:
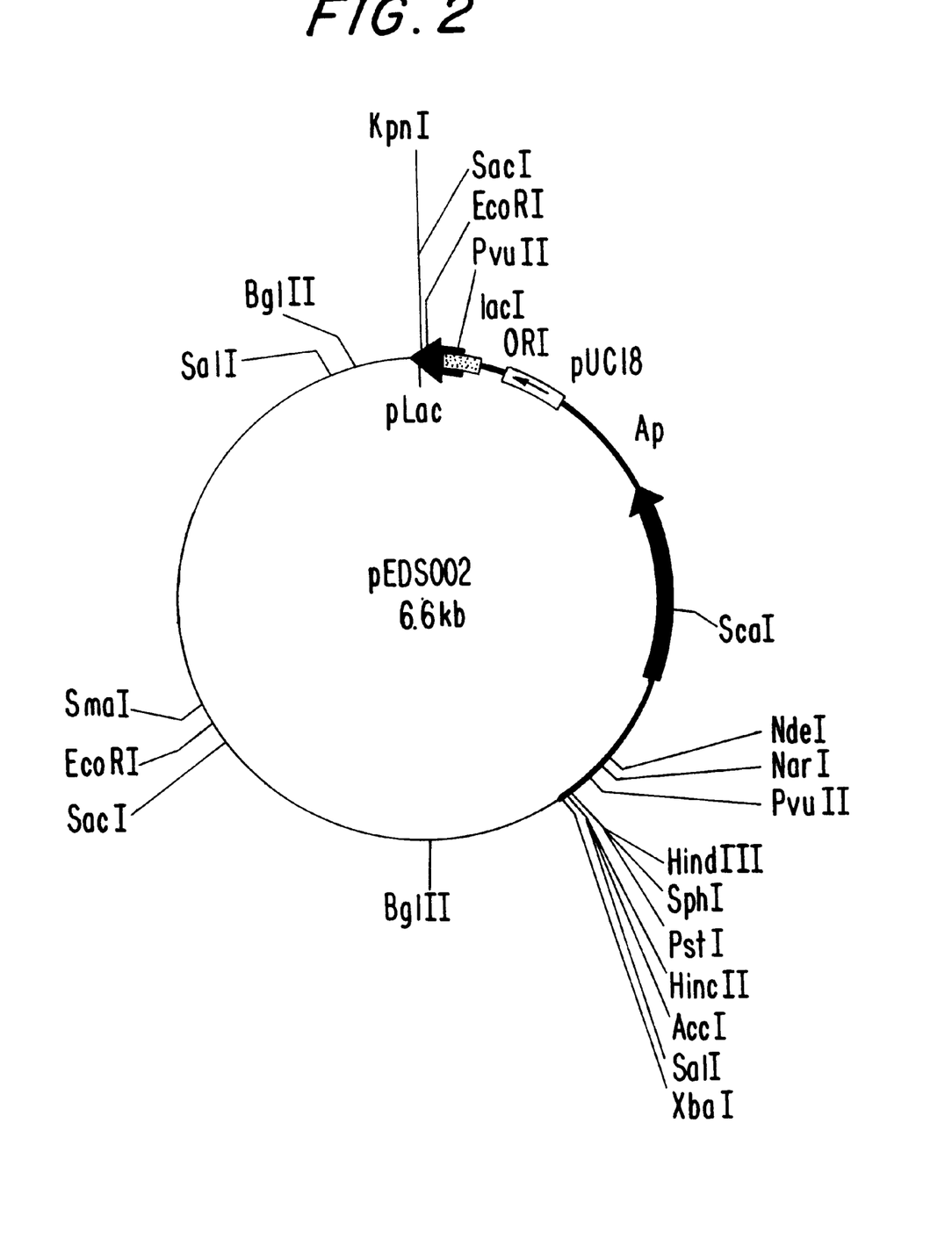
FIG. 2 is a restriction map for plasmid pEDS002. Plasmid PEDS002 has been obtained by inserting into pUC18 an approximately 3.9 kb fragment obtained by digesting plasmid pEDS001 with restriction enzymes KpnI and BamHI.
Figure 3:
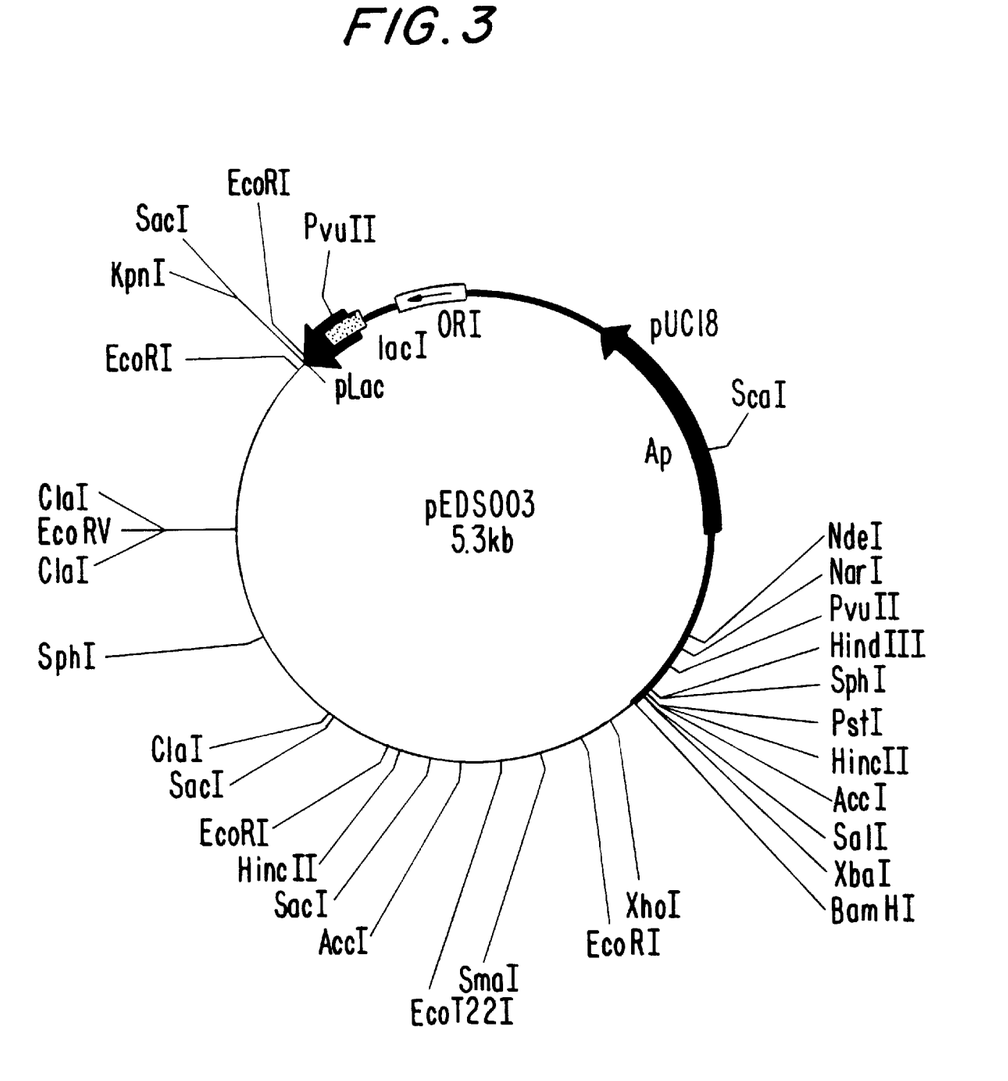
FIG. 3 is a restriction map for plasmid pEDS003. Plasmid pEDS003 has been obtained by inserting into pUC18 an approximately 2.6 kb fragment obtained by digesting plasmid pEDS001 with restriction enzymes KpnI and BamHI.

(8) Preparation of Restriction Map and Identification of the Ethylenediamine-N,N'-Disuccinic Acid:Ethylenediamine Lyase Gene Region Plasmid pEDS001 from step (7) above was digested with several restriction enzymes to prepare a restriction map (FIG. 1). Furthermore, subcloning was conducted in a conventional manner. Briefly, pEDS001 was digested with restriction enzymes KpnI and BamHI. The resultant fragments were ligated to pUC18 which had been digested with the same enzymes. E. coli strain JM109 was transformed with the ligation solution to yield a plasmid having an approx. 3.9 kb insert (pEDS002) (FIG. 2) and a plasmid having an approx. 2.6 kb insert (pEDS003) (FIG. 3). Each of these plasmids was digested with restriction enzymes BamHI, EcoRI, SacI, SacII, etc. and subjected to agarose gel electrophoresis. A fragment with which the probes hybridize was selected by Southern hybridization.

(9) Determination of Nucleotide Sequences

Nucleotide sequences of regions around the region identified in step (8) were determined with a Pharmacia fluorescent sequencer, ALFII. As a result, the nucleotide sequence of SEQ ID NO: 2 was obtained, and an open reading frame having the amino acid sequence of SEQ ID NO: 1 was found therein. The search using the amino acid sequence database NBRF (National Biomedical Research Foundation) revealed that this gene has 20–30% homology to delta-crystallin gene or argininosuccinate lyase gene. Both of these enzymes are known to have an activity of catalyzing condensation or decomposition reaction of fumaric acid and an amine (amino acid). The nucleotide sequence of the open reading frame is shown in SEQ ID NO. 3.

EXAMPLE 2

To 2 μl of the recombinant plasmid pEDS003 from step (7) in Example 1 which contains the ethylenediamine-N,N'-disuccinic acid: ethylenediamine lyase gene, 2 μl of a 10×restriction enzyme buffer, 15 μl of sterilized water and 1 μl of restriction enzyme KpnI were added and the mixture was reacted at 37° C. for 2 hours. The plasmid was recovered by ethanol precipitation and dried. Then, 17 μl of sterilized water, 2 μl of a 10×restriction enzyme buffer and 1 μl of restriction enzyme BamHI were added thereto and the mixture was reacted at 37° C. for 2 hours. From the reaction solution, an approx. 2.6 kb fragment was separated by agarose gel electrophoresis and inserted into vector pUC119 for E. coli. Using this ligation solution, E. coli strain JM109 was transformed to yield a plasmid of interest. The thus prepared plasmid was designated pEDS020 and the transformant, JM109/pEDS020.

The transformant, JM109/pEDS020 was inoculated into 1 ml of an LB medium containing 50 mg/l of ampicillin and cultured at 37° C. for 8 hours with shaking. Then, the cells were cultured in 40 ml of an LB medium (containing 50 mg/l of ampicillin and 1 mM isopropyl-β-thiogalactoside) at 37° C. for 30 hours. The resultant culture was washed with a 10 mM sodium phosphate buffer (pH 8.0) and then suspended in 2 ml of the same buffer. An aliquot of the resultant cell suspension was suspended in 50 ml of an aqueous solution (pH 8.0) containing 342 mM fumaric acid and 171 mM ethylenediamine, and the suspension was reacted for 24 hours. After cells had been removed from the reaction solution by centrifugation, the presence of ethylenediamine-N,N'-disuccinic acid was confirmed by HPLC [WAKOSIL 5C8 from Wako Pure Chemical Industries (eluent: 50 mM phosphoric acid solution containing 10 mM tetra-n-butylammonium hydroxide and 0.4 mM $CuSO_4$, pH 2)]. As a result, it was found that 50 mM S,S-ethylenediamine-N,N'-disuccinic acid was produced.

Figure 4:
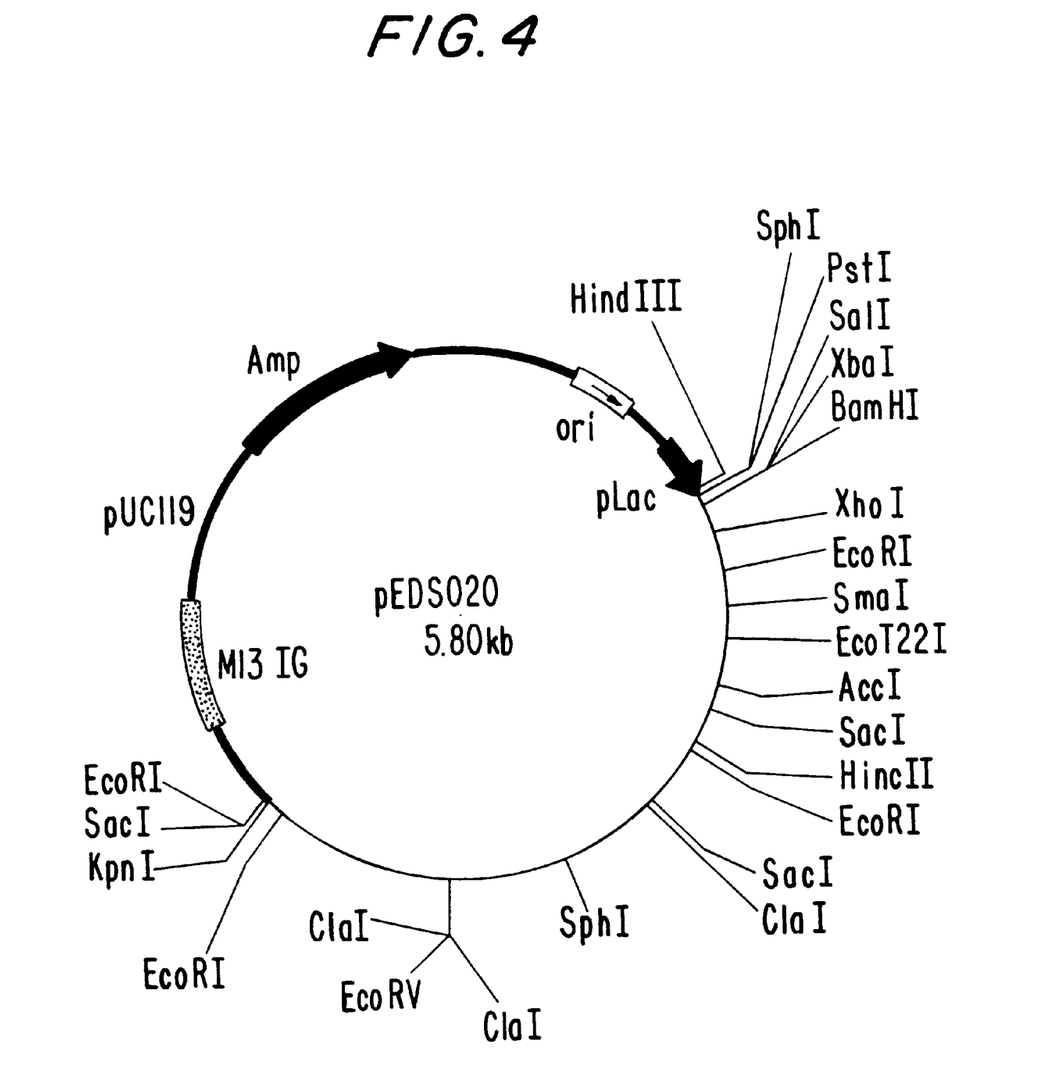
FIG. 4 is a restriction map for plasmid pEDS020. Plasmid pEDS020 has been obtained by inserting into pUC119 an approximately 2.6 kb fragment obtained by digesting plasmid pEDS003 with restriction enzymes KpnI and BamHI.

Plasmid pEDS020 (FIG. 4) containing the ethylenediamine-N,N'-disuccinic acid:ethylenediamine lyase gene has been deposited with the National Institute of Bioscience and Human-technology, Agency of Industrial Science and Technology under Accession No. FERM BP-6161 as being incorporated in transformant *E. coli* JM109/pEDS020.

Having set forth the general nature and specific embodiments of the present invention, the true scope of the present invention is now particularly pointed out in the appended claims.

What is claimed is:

1. An isolated DNA comprising a nucleotide sequence coding for a polypeptide having ethylenediamine-N,N'-disuccinic acid:ethylenediamine lyase activity, said polypeptide comprising the sequence of SEQ ID NO: 1.

2. The DNA of claim 1, wherein the nucleotide sequence coding for the polypeptide comprises the nucleotide sequence of SEQ ID NO: 2.

3. An isolated DNA comprising a nucleotide sequence coding for a polypeptide having ethylenediamine-N,N'-disuccinic acid:ethylenediamine lyase activity, wherein said polypeptide comprises the sequence of SEQ ID NO: 1 containing a deletion, substitution or addition of one amino acid.

4. A synthetic DNA for use s a primer to isolate DNA encoding ethylenediamine-N,N'-disuccinic acid:ethylenediamine lyase comprising the nucleotide sequence of SEQ ID NO: 4 or 5.

5. A DNA fragment of 200–350 bp which results from the PCR amplification of genomic DNA using the synthetic DNA of claim 4 as a primer, wherein said genomic DNA is isolated from Brevundimonas sp. TN-3 (FERM BP-5886).

6. A recombinant plasmid containing the DNA of claim 1.

7. A recombinant plasmid containing the DNA of claim 2.

8. A host cell tansformed with the recombinant plasmid of claim 6.

9. A host transformed with the recombinant plasmid of claim 7.

10. The transformed host cell of claim 8, which is a microorganism.

11. The transformed host cell of claim 9, which is a microorganism.

* * * * *

UNITED STATES PATENT AND TRADEMARK OFFICE
CERTIFICATE OF CORRECTION

PATENT NO. : 6,168,940 B1
DATED : January 2, 2001
INVENTOR(S) : Wataru Mizunashi It is certified that error appears in the above-identified patent and that said Letters Patent is hereby corrected as shown below:

Title page,
Item [73], should read as follows:
-- Assignees: Mitsubishi Rayon Co., Ltd., Tokyo, Japan --

Signed and Sealed this

Twelfth Day of March, 2002

Attest:

*Attesting Officer*

JAMES E. ROGAN
*Director of the United States Patent and Trademark Office*